United States Patent [19]

Bessin

[11] 4,148,911
[45] Apr. 10, 1979

[54] METHOD OF TREATING RESPIRATORY DISORDERS

[75] Inventor: Pierre Bessin, Chilly Mazarin, France

[73] Assignee: Societe Anonyme Dite Albert Rolland S.A., Paris, France

[21] Appl. No.: 814,108

[22] Filed: Jul. 8, 1977

[51] Int. Cl.² .................... A61K 27/00; A61K 31/34; A61K 31/40; A61K 31/445
[52] U.S. Cl. .............................. 424/285; 424/248.51; 424/248.56; 424/267; 424/274; 424/275
[58] Field of Search ........................................ 424/285

[56] References Cited
U.S. PATENT DOCUMENTS 4,029,808   6/1977   Thuillier et al. .................. 424/275

Primary Examiner—Stanley J. Friedman

[57] ABSTRACT

The present invention relates to a method of treating chronic or non-chronic respiratory disorders, consisting in administering to the patient by the oral, rectal or parenteral route, a medicament for dilating the bronchi, comprising as active ingredient at least one compound of formula I or one of its pharmaceutically acceptable salts:

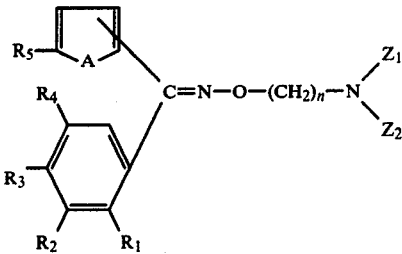

I in which A represents O or S, $R_1$, $R_2$, $R_3$, $R_4$ represent the hydrogen atom, an atom of halogen, an alkyl group with 1 to 4 carbon atoms or an alkoxy or alkenyloxy group, $Z_1$ and $Z_2$ represent an alkyl group or form with the nitrogen atom to which they are attached a saturated heterocyclic compound such as, in particular, pyrrolidine, piperidine, morpholine.

3 Claims, No Drawings

METHOD OF TREATING RESPIRATORY DISORDERS

The present invention relates to novel broncho-dilator medicaments, of which the active ingredients are basic ethers of oximes and to a novel method of treating respiratory disorders, which consists in administering said novel medicaments in order to dilate the patient's bronchi.

The active ingredients used according to the present invention correspond to general formula I:

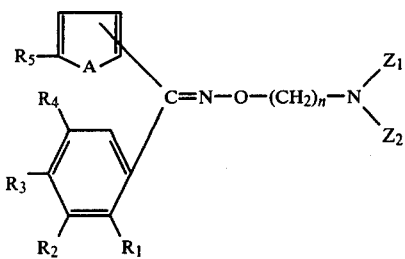

in which A represents O or S, $R_1, R_2, R_3, R_4$ represent the hydrogen atom, an atom of halogen, an alkyl group having 1 to 4 carbon atoms or an alkoxy or alkenyloxy group, $Z_1$ and $Z_2$ represent an alkyl group, or form with the nitrogen atom to which they are attached a saturated heterocyclic compound such as, in particular, pyrrolidine, piperidine, morpholine.

It is known that, in the case of oximes, two compounds, geometric isomers, correspond to the same structural formula and the present invention concerns both the mixtures of the two isomers and each of them taken separately, as well as the salts which these amines form with pharmaceutically acceptable acids.

These oxime ethers and the processes for preparing them are described in co-pending U.S. Ser. No. 515,063, which mentions that these compounds have been the object of a pharmacological study which demonstrated their coronary vaso-dilator and anti-spasmodic activity, as well as their action on the rate and intensity of the cardiac contractions, with the result that they may be used for the treatment of cardiopathies.

It has now been unexpectedly found that these compounds also have a broncho-dilator activity; they therefore represent an effective means of treating patients having respiratory difficulties associated, or not, with a cardiopathy. Their interest is obvious for the treatment of patients in whom the broncho-dilators which act by stimulating the $\beta$-receptors of the sympathetic system, trigger off attacks of tachycardia.

The broncho-dilator preparations containing the compounds of the invention in the form of tablets, injectable solutions, suppositories or sprays associated with known excipients, will be administered at non-toxic unitary doses, as a function of the symptoms to be treated and included between 1 mg and 100 mg, for treating the disorders of the respiratory tracts, which may or may not be chronic, such as asthma, bronchitis, dyspnoea.

Examples of the results obtained during the pharmacological study of the broncho-dilator activity of the compounds, made on an isolated organ, are indicated hereinafter; they are compared with those of theophylline and isoprenaline, which are known broncho-dilators.

In these tests, the trachea of a guinea pig was used, which was removed after sacrifice of the animal and cut in a physiological medium into regular rings which were then connected by means of a fine thread ligature; the organ was suspended in a constantly aerated bath of Krebs solution, at 37° C.

The spontaneous relaxation of the organ is studied when introduced in the substance to be tested at a concentration of 1.33 mcg/ml for the compounds of the invention, 1.5 mg/ml for theophylline and 0.003 mcg/ml for isoprenaline. The results are shown in Table I. It should be noted that the two isomers of oxime ethers have greater broncho-dilator effects than those of theophylline, since they act at a dose which is 1000 times weaker in a test which demonstrates the relaxing action of the substance on the bronchial muscle, that they are less effective than isoprenaline but are of greater interest than this substance whose action on the parasympathetic system causes undesirable secondary effects.

These studies in vitro were completed by tests in vivo. For the compound of Example 9 at the dose of 50 to 250 mcg/kg, there is obtained in the anaesthetized rat a broncho-dilator activity which is longer-lasting than that of the isoprenaline administered intravenously at a dose of 0.5 to 2 mcg/kg and without increase in the heart rate.

The broncho-dilator medicaments of this invention are prepared by conventional methods and the following non-limiting examples give the composition of pharmaceutical forms which may be produced:

| Tablets | |
|---|---|
| Compound of Example 9 | 5 mg |
| Starch | 5 mg |
| Microcrystalline cellulose | 75 mg |

These tablets may be coated and all the usual excipients may be used for this pharmaceutical form, the content of active ingredient being from 1 mg to 50 mg.

Flasks of lyophilized compound for injectable preparations containing from 10 to 100 mg of active ingredient with the sufficient quantity of glycine, to obtain 5 ml of isotonic solution by dilution in water just before injection.

TABLE I

| Example No | Structural Formula | Salt: MP° C. (nature of the acid) | % * Isomer E | Intensity of the decontraction of the organ |
|---|---|---|---|---|
| 1 | thiophene-C(=N-O-(CH₂)₂-N(C₂H₅)₂)-(2,3-diCl-4-OCH₃-phenyl) | 158 (HCl) | 45 | slight |
| 1bis | thiophene-C(=N-O-(CH₂)₂-N(C₂H₅)₂)-(2,3-diCl-4-OCH₃-phenyl) | 184 (HCl) | 0 | average |
| 2 | thiophene-C(=N-O-(CH₂)₂-N(CH₃)₂)-(2,3-diCl-4-OCH₃-phenyl) | 160 (HCl) | 0 | strong |
| 3 | thiophene-C(=N-O-(CH₂)₂-morpholino)-(2,3-diCl-4-OCH₃-phenyl) | 248 (HCl) | 90 | average |
| 3bis | thiophene-C(=N-O-(CH₂)₂-morpholino)-(2,3-diCl-4-OCH₃-phenyl) | 237 (HCl) | 0 | average |
| 4 | thiophene-C(=N-O-(CH₂)₃-N(CH₃)₂)-(2,3-diCl-4-OCH₃-phenyl) | 179 (HCl) | 80 | average |
| 5 | (5-Cl-thiophene)-C(=N-O-(CH₂)₂-N(C₂H₅)₂)-(2,3-diCl-4-OCH₃-phenyl) | 155 (HCl) | 45 | average |
| 6 | thiophene-C(=N-O-(CH₂)₂-N(C₂H₅)₂)-(3,4,5-triOCH₃-phenyl) | 183 (HCl) | 0 | average |

TABLE I-continued

| Example No | Structural Formula | Salt: MP° C. (nature of the acid) | % * Isomer E | Intensity of the decontraction of the organ |
|---|---|---|---|---|
| 7 | thiophene-C(=N-O-(CH$_2$)$_2$-N(C$_2$H$_5$)$_2$)-C$_6$H$_3$(OCH$_3$)(OCH$_3$) | 128 (HCl) | 40 | strong |
| 8 | thiophene-C(=N-O-(CH$_2$)$_2$-N(C$_2$H$_5$)$_2$)-C$_6$H$_4$(Cl) | 138 (HCl) | 75 | strong |
| 9 | furan-C(=N-O-(CH$_2$)$_2$-N(C$_2$H$_5$)$_2$)-C$_6$H$_2$(Cl)(Cl)(OCH$_3$) | 146 (CH$_3$SO$_3$H) | 100 | strong |
| 9bis | furan-C(=N-O-(CH$_2$)$_2$-N(C$_2$H$_5$)$_2$)-C$_6$H$_2$(Cl)(Cl)(OCH$_3$) | 146 (HCl) | 0 | strong |
| 10 | furan-C(=N-O-(CH$_2$)$_2$-N(CH$_3$)$_2$)-C$_6$H$_2$(Cl)(Cl)(OCH$_3$) | 180 (HCl) | 75 | strong |
| 11 | furan-C(=N-O-(CH$_2$)$_3$-N(CH$_3$)$_2$)-C$_6$H$_2$(Cl)(Cl)(OCH$_3$) | 146 (HCl) | 65 | slight |
| 12 | furan-C(=N-O-(CH$_2$)$_2$-N(pyrrolidine))-C$_6$H$_2$(Cl)(Cl)(OCH$_3$) | 161 | 70 | strong |
| 13 | furan-C(=N-O-(CH$_2$)$_2$-N(C$_2$H$_5$)$_2$)-C$_6$H$_3$(Cl)(OCH$_3$) | 120 (fumarate) | 90 | strong |

TABLE I-continued

| Example No | Structural Formula | Salt: MP° C. (nature of the acid) | % * Isomer E | Intensity of the decontraction of the organ |
|---|---|---|---|---|
| 14 | (furan)–C(=N–O–(CH$_2$)$_2$–N(C$_2$H$_5$)$_2$)–(2,3-Cl$_2$-4-OC$_2$H$_5$-phenyl) | 131 (HCl) | 90 | strong |
| 15 | (furan)–C(=N–O–(CH$_2$)$_2$–N(C$_2$H$_5$)$_2$)–phenyl | 159 (HCl) | 0 | very strong |
| 16 | (thiophene)–C(=N–O–(CH$_2$)$_2$–N(C$_2$H$_5$)$_2$)–(2,3-Cl$_2$-4-OCH$_3$-phenyl) | 135 (HCl) | 65 | average |
| 17 Isoprenaline | HO–(3,4-(OH)$_2$-phenyl)–CH(OH)–CH$_2$–NHCH(CH$_3$)$_2$ | | | strong |
| 18 Theophylline | (theophylline structure) | | | strong |

* "E" being the nomenclature of the isomers of oximes defined by IUPAC

What is claimed is:

1. A method of treating respiratory disorders consisting of administering an effective amount of a compound having the formula

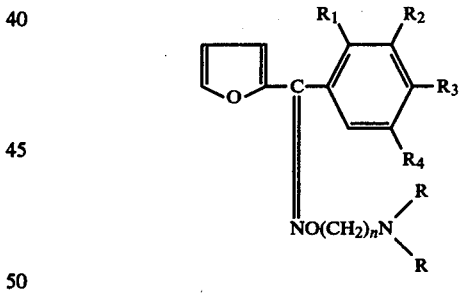

wherein $R_1$, $R_2$, $R_3$, $R_4$ are selected from hydrogen, an atom of halogen, an alkyl group with 1 to 4 carbon atoms and an alkoxy group with 1 to 4 carbon atoms and R is an alkyl group with 1 to 4 carbon atoms, to said man.

2. Method of treating respiratory disorders in man consisting in administering a medicament containing a therapeutically effective amount of at least one of the two stereoisomers of (2,3-dichloro-4-methoxy) phenyl-2-furyl O-(dimethylaminoethyl) ketone oxime or a pharmaceutically acceptable acid salt thereof to said man.

3. The method of treatment of claim 2, whereby the active ingredient is administered orally in the form of tablets, gelatin-coated tablets or aerosols or by the parenteral route at daily doses of between 5 and 200 mg.

* * * * *